United States Patent [19]

Anthony

[11] Patent Number: 5,435,298
[45] Date of Patent: Jul. 25, 1995

[54] DEVICE FOR COMPENSATING FOR THE MOISTURE AND HEAT LOSSES FROM AN ARTIFICIAL NOSE

[75] Inventor: Jean-Michel Anthony, Wilrijk, Belgium

[73] Assignee: Ponnet, Gilman en Anthony, Kapellen, Belgium

[21] Appl. No.: 960,412

[22] PCT Filed: Jun. 17, 1991

[86] PCT No.: PCT/BE91/00038
§ 371 Date: Jan. 15, 1993
§ 102(e) Date: Jan. 15, 1993

[87] PCT Pub. No.: WO91/19527
PCT Pub. Date: Dec. 26, 1991

[30] Foreign Application Priority Data

Jun. 18, 1990 [BE] Belgium ............................ 09000619
Dec. 14, 1990 [BE] Belgium ............................ 090011.98

[51] Int. Cl.⁶ .................. A62B 18/08; A62B 7/00; A61M 16/10; F24J 3/00
[52] U.S. Cl. .................... 128/201.13; 128/204.17; 128/203.16; 128/203.17
[58] Field of Search .............. 128/201.13, 203.12, 128/203.26, 203.27, 203.16, 203.17, 204.13, 204.17, 205.12

[56] References Cited

U.S. PATENT DOCUMENTS

| | | | |
|---|---|---|---|
| 3,163,707 | 12/1964 | Darling | 128/204.18 |
| 3,912,795 | 10/1975 | Jackson | 128/207.14 |
| 4,007,737 | 2/1977 | Paluch | 128/201.13 |
| 4,048,993 | 9/1977 | Dobritz | 128/201.13 |
| 4,090,513 | 5/1978 | Togawa | 128/201.13 |
| 4,200,094 | 4/1980 | Gedeon et al. | 128/201.13 |
| 4,363,238 | 12/1982 | Willam | 73/204 |
| 4,516,573 | 4/1985 | Gedeon | 128/201.13 |
| 4,620,537 | 11/1986 | Brown | 128/201.13 |
| 4,771,770 | 9/1988 | Artemenko et al. | 128/201.13 |
| 5,172,686 | 12/1992 | Anthony | 128/201.13 |

FOREIGN PATENT DOCUMENTS

| | | | |
|---|---|---|---|
| 320839 | 2/1975 | Austria . | |
| 0201985 | 11/1986 | European Pat. Off. . | |
| 0258928 | 3/1988 | European Pat. Off. . | |
| 0265163 | 4/1988 | European Pat. Off. | 128/201.13 |
| 413127 | 7/1990 | European Pat. Off. | 128/201.13 |
| 567158 | 10/1993 | European Pat. Off. | 128/201.13 |
| 2304359 | 10/1976 | France . | |
| 3311811 | 10/1984 | Germany . | |
| 3818070 | 12/1989 | Germany . | |
| 1424623 | 2/1976 | United Kingdom . | |
| 2176405 | 12/1986 | United Kingdom . | |
| 9207601 | 5/1992 | WIPO | 128/201.13 |

Primary Examiner—Kimberly L. Ahser
Attorney, Agent, or Firm—Fitch, Even, Tabin & Flannery

[57] ABSTRACT

A device for compensating for the moisture and heat losses from an artificial nose used with a patient, which device is provided to be incorporated in the duct for supplying air and/or gasses to a patient and which is composed of a chamber (1) used as actual artificial nose wherein a hygroscopic material (7) serving as a buffer is provided, with means being provided to maintain the air in- and exhaled by the patient, at the required heat level, between the artificial nose and the patient. FIG. 1.

19 Claims, 2 Drawing Sheets

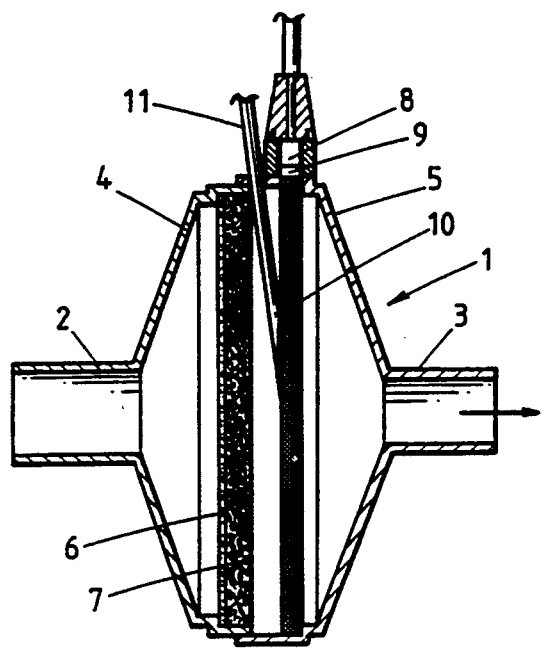
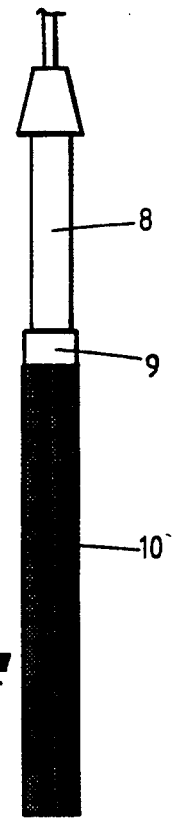
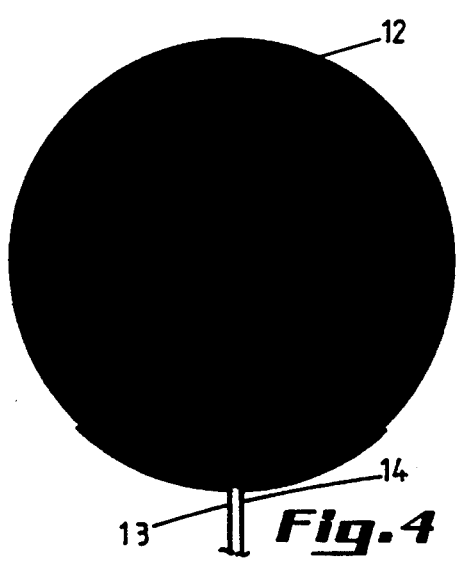
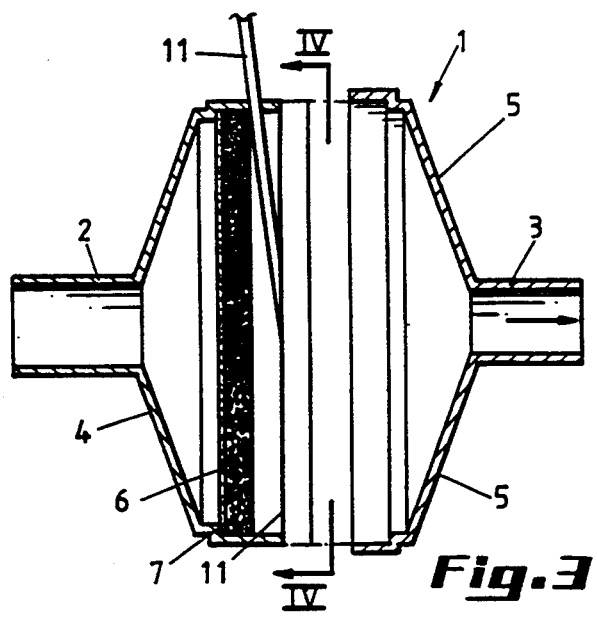

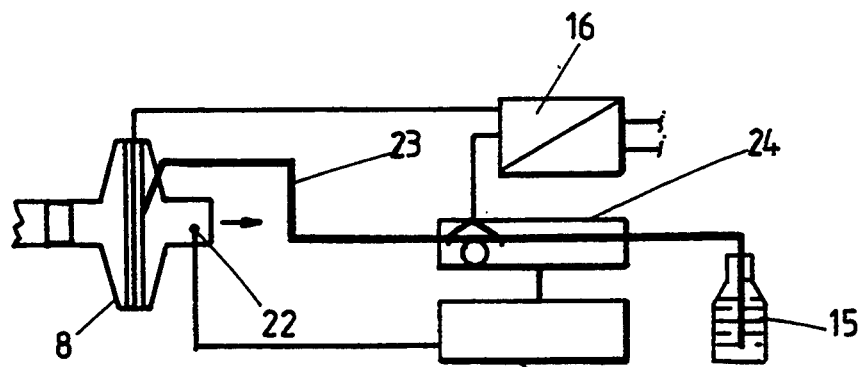

DEVICE FOR COMPENSATING FOR THE MOISTURE AND HEAT LOSSES FROM AN ARTIFICIAL NOSE

This invention relates to an artificial nose device.

Artificial noses are devices which are incorporated in a duct between a patient and a machine, usually known as a ventilator, in order to allow the patient to recuperate a portion of the moisture and heat comprised in his exhaled air. Artificial noses are mainly used for anesthesia and/or for artificial respiration, such artificial noses including a buffer, i.e. the moisture exchanger element, generally called HME. An example of such an artificial nose is described in FFR-A-2304359.

In many cases, such a device is not sufficient for maintaining the humidity and the temperature on the desired level.

Indeed, different types of artificial noses have the very series drawback of involving, in the most advantageous circumstances, a moisture and heat loss of about 30%. The temperature of gas supplied to the patient can be raised by means of an electrically-heated delivery hose of the kind described in EP-A-0201985 but such a hose is relatively expensive and not, therefore, suitable for single-use as generally preferred.

Therefore, an object of the invention is to prescribe a device which solves the hereabove mentioned problem in a reliable way and which assures therefore the required humidity and temperature level of the air and/or mixture of air and gasses supplied to the patient, whatever may be the shortcomings of the artificial nose which is also known in the technical jargon as "heat moisture exchanger or HME".

In order to realize this according to the invention, the device according to the invention is provided to be incorporated in the duct for supplying air and/or gasses to a patient and is composed of a chamber used as actual artificial nose wherein a hygroscopic material serving as a buffer is provided, with means being provided to maintain the air in- and exhaled by the patient, at the required temperature level, between the artificial nose and the patient.

In the most advantageous embodiment, said means is an electrical resistance heater which is positioned at a distance from said hygroscopic material.

According to a possible embodiment, said electrical resistance heater is mounted in said chamber.

According to a possible variant, said electrical resistance heater is mounted outside said chamber, between this chamber and the patient.

It is advisable that said electrical resistance heater is enclosed within an external water-absorbent material and that means are provided for supplying water to this material.

According to a possible embodiment, said electrical resistance heater has e metal sleeve enclosed within an external water-absorbent material.

According to another possible embodiment, said resistance is composed of a textile, at least a part of the weft and/or warp threads of which consist of heating resistances.

Other details and advantages of the invention will become apparent from the following description of a device for compensating for the moisture and heat losses from an artificial nose used with a patient according to the invention. This description is only given by way of example and does not limit the invention. The reference numerals relate to the annexed figures.

FIG. 1 is a longitudinal sectional view through the device according to the invention.

FIG. 2 is, on a larger scale, a side elevation view of a heating resistance according to a first possible embodiment.

FIG. 3 is a longitudinal sectional view through a variant of the invention with disassembled components.

FIG. 4 is a front elevation view of a cross-section according to line IV-IV in FIG. 3 of a resistance according to a variant.

FIGS. 5, 6 and 7 show schematically three possible arrangements of a pump and a container with water in a device according to the invention.

The device according to FIG. 1 consists of a chamber 1 with two mouthpieces 2 and 3 which are connected to a not represented duct to a machine (a ventilator is usually meant here).

The function of an artificial nose (in the technical jargon usually called HME) has been described in broad outline in the introductory portion.

The device by which the heat and moisture losses from an artificial nose can be compensated for, consists therefore of a chambre 1 which can be realized for example by coupling two halves 4 and 5 to which the already mentioned mouthpieces 2 and 3 are connected. Since in normal conditions, i.e. when the air circulates from the left to the right (according to FIGS. 1 and 3) or vice-versa, the mouthpieces 2 and 3 can be considered alternatively as an inlet and outlet for the air circulating through said chamber. Referring to FIGS. 3 and 5-7, the patient is located in the direction indicated by a small arrow.

In the supposition that the artificial nose is located in the device at the side of mouthpiece 2, the following succession of components can be seen successively in chamber 1:

a) a bacterial filter 6 b) a hygroscopic material 7 causing a buffer effect. The shape of the hygroscopic material 7 is adapted to the cross-section of chamber 1. In this case the shape of a disk. Each material with important hygroscopic properties can be used herefor. Use can be made of a spongy material or of corrugated paper to which a hygroscopic substance has been added;

c) a resistance 8, which projects into a metal sleeve 9, is provided at a clear distance from the disk of hygroscopic material 7. Such a sleeve can best be made of aluminium. Although this is not essentially required, it is advisable that a water-absorbent material 10 is applied substantially over the whole length of sleeve 9. A textile can be used hereto but the metal sleeve 9 may be covered with a water-absorbent material. Water is then supplied to the water-absorbent material 10 either directly by gravitation or by means of a pump and this through a duct 11.

The hereabove under c) mentioned resistance 8 is a self-regulating resistance capable of maintaining a substantially constant temperature with a 12 V source.

In a variant, the self-regulating resistance may be present in the shape of a disk 12 (FIGS. 3 and 4). Such a disk is cut out of a textile, some of the warp and/or weft threads of which are electrically conductive. The current can be supplied in the way shown in FIG. 4, where two conductors 13 and 14 are provided in an arc-shape over a part of the disk. In the supposition that the resistance threads are arranged vertically (according to FIG. 4), there will be tension mainly on a vertical middle-strip. If necessary, water can be supplied through a duct 11 to this disk 12 or to the middle-strip of the latter.

The structure of the electrically conductive threads as well as of the other threads allows a regular distribution and therefore also a regular evaporation of the water.

The disk 12 can be clamped between the two halves 4 and 5 composing the chamber 1 or can be fixed to the wall of halve 5 by any appropriate technique known per se.

By a standard choice of the resistances, as well of these which have the shape as shown by FIGS. 1 and 2, as of those which have the shape of disk 12, and by dosing the amount of water reaching these resistance through duct 11 according to the needs, the temperature as well as the humidity of the air inhaled by the patient through the artificial nose can be maintained at the desired level by evaporation.

Supplying water is not essentially required. The hygroscopic material provides for a buffer effect which optimizes the humidity of the circulating air. By heating the air, a larger amount of moisture will condense and will be absorbed by the hygroscopic material so that the moisture loss will be reduced to an acceptable minimum.

Therefore, heat and moisture losses in the artificial nose can be compensated for by technically reliable means which are easy to control.

The buffer effect caused by the hygroscopic material 7, is considerably increased by the presence of a self-regulating resistance according to one of the two hereabove described embodiments at a distance from this material. These resistances are either positive temperature coefficient (PTC)- or negative temperature coefficient (NTC)-resistances.

Still according to the spirit of the invention, the here described resistances of the type according to FIG. 2 or according to FIG. 4, can be mounted completely outside chamber 1. In this case, chamber 1 with the hygroscopic material 7 and the bacterial filter 6 is reduced to the actual artificial nose. The resistance covered by the textile which is in contact with this resistance through the aluminum sleeve 9, or the resistance from the textile which forms the disk 12 and to which water is supplied, is then incorporated in the duct, which has already been put forward hereinabove, between the artificial nose and the patient. When the buffer effect of the hygroscopic material 7 fails or falls out, the effects of the resistance of the type according to FIGS. 1 and 2 or of the type according to FIG. 4 will compensate for the moisture and heat losses in a satisfactory way.

In the device according to the invention, the moisture supply through duct 23 can be dosed by means of a pump 24 which receives the moisture from a container 15. A transformer 16 supplies a low-voltage current to resistance 8, 12, to pump 24 as well as to a programmable unit 17. The programmable unit 7 receives signals from a quick reacting temperature sensor 22 (FIG. 5-7) which detects the flow and the flow times of the air supplied to a patient. The pump 24 may run also continuously at an adjustable flow rate which is situated in practice between 2 and 10 ml/hour. Pump 24 may be omitted if the moisture supply is realized by gravitation as shown by FIG. 6. In such a variant embodiment, a squeeze-valve 18 is mounted in the water supply duct 23'. The water is delivered from a receiver 19. In this case, programmable unit 17 responds to the squeeze-valve 18.

Finally, moisture (usually water is meant hereby) can be supplied by capillarity to a resistance (for example 8). A possible embodiment based on this principle is shown in FIG. 7, wherein a wick 20 supplies the moisture from a container 21 to the resistance 8.

From the hereabove description of the device according to the invention, it is therefore apparent that an excellent solution is provided, by technically simple but reliable means, for the problem consisting in assuring the heat and moisture level in or in combination with an artificial nose.

What is claimed is:

1. An artificial nose device for supplying gas to an inhaling and exhaling patient under controlled moisture and temperature conditions, the device comprising:
   a chamber defining a single flow path for conveying both patient inhalations and patient exhalations;
   a heat and moisture exchange element comprised of a hygroscopic material mounted in the chamber and positioned within said flow path;
   a first opening in the chamber in fluid communication with the heat and moisture exchange element;
   a second opening in the chamber in fluid communication with the heat and moisture exchange element and adapted for communication with inhalations and exhalations of the patient such that breath exhaled by the patient enters the chamber through the second opening and passes through the heat and moisture exchange element in a first direction before exiting the chamber through the first opening, and gas inhaled by the patient enters the chamber through the first opening and passes through the heat and moisture exchange element in a second direction before being drawn through the second opening;
   said heat and moisture exchange element comprising means for retaining at least a portion of the heat and moisture of the exhaled breath passing through the exchange element in said first direction, and for releasing at least a portion of the heat and moisture retained from the exhaled breath to the inhaled gas passing through the exchange element in said second direction; and
   a heater disposed in the single flow path connected to an external source of energy to generate heat between the heat and moisture exchange element and a patient outlet in direct fluid communication with said second opening for heating both the inhaled gas and the exhaled breath of the patient by substantially direct thermal contact therewith.

2. The device as claimed in claim 1, wherein said heater comprises an electrical resistance heater which is located at a distance from said hygroscopic material.

3. The device as claimed in claim 1, wherein said heater comprises an electrical resistance heater which is in contact with said hygroscopic material.

4. The device as claimed in claim 3, wherein said electrical resistance heater is mounted in said chamber.

5. The device as claimed in claim 1, wherein said heater comprises a self-regulating heating resistance.

6. The device as claimed in claim 1, wherein said heater comprises an electrical resistance heater enclosed within an external water-absorbent material, and wherein means are provided for supplying water to the water absorbent material.

7. The device as claimed in claim 6, wherein said electrical resistance heater has a metal sleeve enclosed within said external water-absorbent material.

8. The device as claimed in claim 7, wherein a water-absorbent textile is applied around the metal sleeve.

9. The device as claimed in claim 7, wherein a water-absorbent material is applied to said metal sleeve.

10. The device as claimed in claim 6, wherein said means for supplying water comprises a water reservoir.

11. The device as claimed in claim 6 comprising means for sensing air flow in the artificial nose and a squeeze-valve, responsive to sensed air flow, for controlling the supply of water to the water-absorbent material.

12. The device as claimed in claim 11, wherein said means for sensing air flow comprises a temperature sensor which detects the flow and the flow time of the air supplied to a patient by a ventilator.

13. The device as claimed in claim 1, wherein said heater comprises a PTC-resistance.

14. The device as claimed in claim 1, wherein said heater comprises a NTC-resistance.

15. The device as claimed in claim 1, wherein said heater comprises a resistance composed of a disk of textile having warp and weft threads, at least a portion of the wrap and/or weft threads of the textile being electrically conductive.

16. The device as claimed in claim 1, wherein said heater comprises an electrical resistance heater provided with a thermostat.

17. An artificial nose device incorporated in a duct for supplying gasses to a patient, which device comprises a chamber wherein a hygroscopic material serving as a buffer is provided, with temperature regulating means being provided between the hygroscopic material and a patient outlet for maintaining gasses inhaled and exhaled by the patient, at a required temperature level;

said temperature regulating means comprising an electrical resistance heater enclosed within an external water-absorbent material;

means for supplying water to said water-absorbent material; and said means for supplying water to said water absorbent material being controlled by a pump and a quick reacting temperature sensor which detects the flow and the flow time of the air supplied to the patient by a ventilator, said pump receiving signals from said temperature sensor representing the detected flow and flow time.

18. The device as claimed in claim 17, comprising a programmable unit responsive to the flow and flow time signals for controlling said pump.

19. The device as claimed in claim 18, comprising means for stopping said pump when no air flow is detected by said temperature sensor during a predetermined time unit.

* * * * *